United States Patent
Jiang et al.

(10) Patent No.: US 7,308,074 B2
(45) Date of Patent: Dec. 11, 2007

(54) MULTI-LAYER REFLECTOR FOR CT DETECTOR

(75) Inventors: Haochuan Jiang, Brookfield, WI (US); David M. Hoffman, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 362 days.

(21) Appl. No.: 10/707,405

(22) Filed: Dec. 11, 2003

(65) Prior Publication Data

US 2005/0129171 A1    Jun. 16, 2005

(51) Int. Cl.
*G01T 1/24* (2006.01)
(52) U.S. Cl. .................... 378/19; 250/370.09
(58) Field of Classification Search .............. 378/19, 378/4, 98.8; 250/370.11, 367, 368, 370.09
See application file for complete search history.

(56) References Cited

U.S. PATENT DOCUMENTS

| | | | | |
|---|---|---|---|---|
| 5,208,460 A * | 5/1993 | Rougeot et al. | ............ | 250/368 |
| 5,378,894 A * | 1/1995 | Akai | ............ | 250/368 |
| 5,519,227 A * | 5/1996 | Karellas | ............ | 250/483.1 |
| 5,773,829 A * | 6/1998 | Iwanczyk et al. | ............ | 250/367 |
| 6,061,419 A * | 5/2000 | Hsieh et al. | ............ | 378/4 |
| 6,285,741 B1 * | 9/2001 | Ackelsberg et al. | ........ | 378/110 |
| 6,473,486 B2 | 10/2002 | Hoffman | | |
| 6,480,562 B2 | 11/2002 | Jiang et al. | | |
| 6,480,563 B2 | 11/2002 | Hoffman et al. | | |
| 6,495,845 B1 * | 12/2002 | Tsunota et al. | ......... | 250/505.1 |
| 6,654,443 B1 | 11/2003 | Hoffman | | |
| 6,898,265 B1 * | 5/2005 | Mliner et al. | ............. | 378/19 |
| 2002/0181647 A1 * | 12/2002 | Venkataramani et al. | ..... | 378/19 |
| 2003/0178570 A1 * | 9/2003 | Tsunota et al. | ........ | 250/370.11 |

* cited by examiner

*Primary Examiner*—Hoon Song
(74) *Attorney, Agent, or Firm*—Ziolkowski Patent Solutions Group, SC (57) ABSTRACT

A multi-layer reflector for a CT detector is disclosed. The reflector includes an x-ray absorption component that is sandwiched between a pair of highly reflective components. Such a reflector is formed between adjacent scintillators of a CT detector so as to reduce cross-talk between adjacent scintillators as well as maintain a relatively high light output for signal detection. Moreover, the multi-layer reflectors may be disposed one-dimensionally or two-dimensionally across a scintillator array. A method of manufacturing such a reflector and incorporating same into a CT detector is also disclosed.

37 Claims, 6 Drawing Sheets

MULTI-LAYER REFLECTOR FOR CT DETECTOR

BACKGROUND OF INVENTION

The present invention relates generally to diagnostic imaging and, more particularly, to a CT detector having a reflector assembly with low cross-talk and high light output. In addition, the present invention relates to a reflector interstitially disposed between scintillators of a scintillator array that reduces cross-talk to improve CT image quality while simultaneously retaining high light output of the scintillators.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

"Cross-talk" between detector cells of a CT detector is common. "Cross-talk" is generally defined as the communication of data between adjacent cells of a CT detector. Generally, cross-talk is sought to be reduced as cross-talk leads to artifact presence in the final reconstructed CT image and contributes to poor spatial resolution. Typically, four difference types of cross-talk may result within a single CT detector. X-ray cross-talk may occur due to x-ray scattering between scintillator cells. Optical cross-talk may occur through the transmission of light through the reflectors that surround the scintillators. Known CT detectors utilize a contiguous optical coupling layer(s), typically epoxy, to secure the scintillator array to the photodiode array. Cross-talk, however, can occur as light from one cell is passed to another through the contiguous layer. Electrical cross-talk can occur from unwanted communication between photodiodes.

Scintillator arrays typically incorporate a reflector layer or coating between adjacent scintillators to limit cross-talk between the scintillators. Generally, the reflector is formed of a material comprising chromium oxide or other types of optically absorbent material to absorb light transmitting across the separation boundaries between scintillators. Because chromium oxide operates as a good absorbent of light, the relative reflectivity of the reflector is reduced, which in some cases may be as much as 60%. As such, incorporating a reflector layer that includes chromium oxide, or similar material, a tradeoff in CT detector design is made between lower cross-talk and reflectivity. If the reflector layer is fabricated without chromium oxide or other optically absorbent materials, cross-talk between scintillators increases. Simply, implementing optically absorbent materials reduces cross-talk but lowers the reflectivity of the reflector.

Reduced reflectivity degrades low signal performance and increased cross-talk affects spatial resolution. Low signal performance is a function of noise generated in the CT detector. As reflectivity falls, the light output of the scintillator also falls. Noise, however, is relatively constant, therefore, decreases in light output increases the ratio of noise to functional light output. Additionally, the amount of cross-talk that may be attributed to scattered x-rays can be estimated to be about 50% of the total cross-talk in the CT detector. While the optically absorbent material is effective in reducing cross-talk associated with the transference of light between scintillators, the reflector typically has poor x-ray absorption characteristics and as such, does not eliminate the x-ray caused cross-talk that may occur between scintillators.

Therefore, it would be desirable to design a CT detector with reduced light and x-ray cross-talk characteristics to improve CT image quality without a sacrifice in light output for improved signal.

BRIEF DESCRIPTION OF INVENTION

The present invention is directed to an apparatus for improving cross-talk reduction in a CT detector without significant reductions in scintillator light output. A method of manufacturing such an apparatus is also disclosed.

A multi-layer reflector for a CT detector is disclosed. The reflector includes an x-ray absorption component that is sandwiched between a pair of highly reflective components. Such a reflector is formed between adjacent scintillators of a CT detector so as to reduce cross-talk between adjacent scintillators as well as maintain a relatively high light output for signal detection. Moreover, the multi-layer reflectors may be disposed one-dimensionally or two-dimensionally across a scintillator array. A method of manufacturing such a reflector and incorporating same into a CT detector is also disclosed.

Therefore, in accordance with one aspect of the present invention, a CT detector includes a scintillator array having a plurality of scintillators and a reflector interstitially disposed between adjacent scintillators. The reflector includes a light absorption element disposed between a pair of reflective elements.

In accordance with another aspect of the present invention, a CT system is provided and includes a CT detector array having a scintillator array configured to illuminate upon reception of radiographic energy. The CT detector array further includes a reflector element disposed between adjacent scintillators of the scintillator array. Each reflector element includes a composite layer sandwiched between at least a pair of reflective layers.

According to another aspect of the present invention, a method of CT detector manufacturing is provided. The method includes the steps of providing a scintillator array of a plurality of scintillators and disposing a reflective layer between adjacent scintillators. The manufacturing method further includes the step of disposing a composite layer in the reflective layer.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
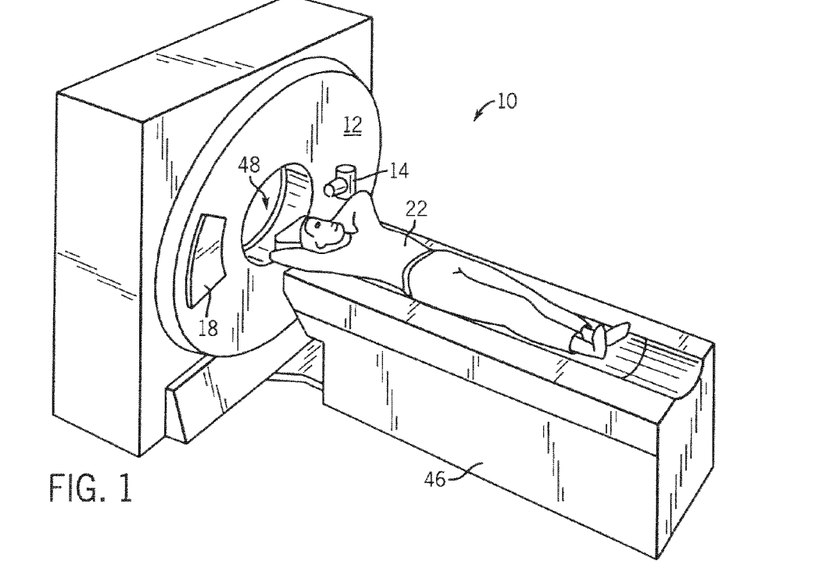
FIG. 1 is a pictorial view of a CT imaging system.
Figure 2:
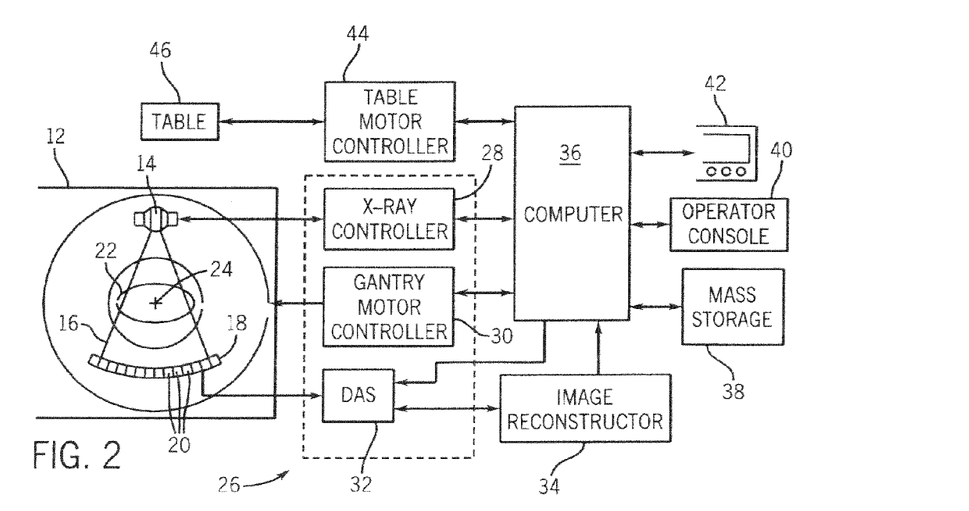
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Figures 3, 4:
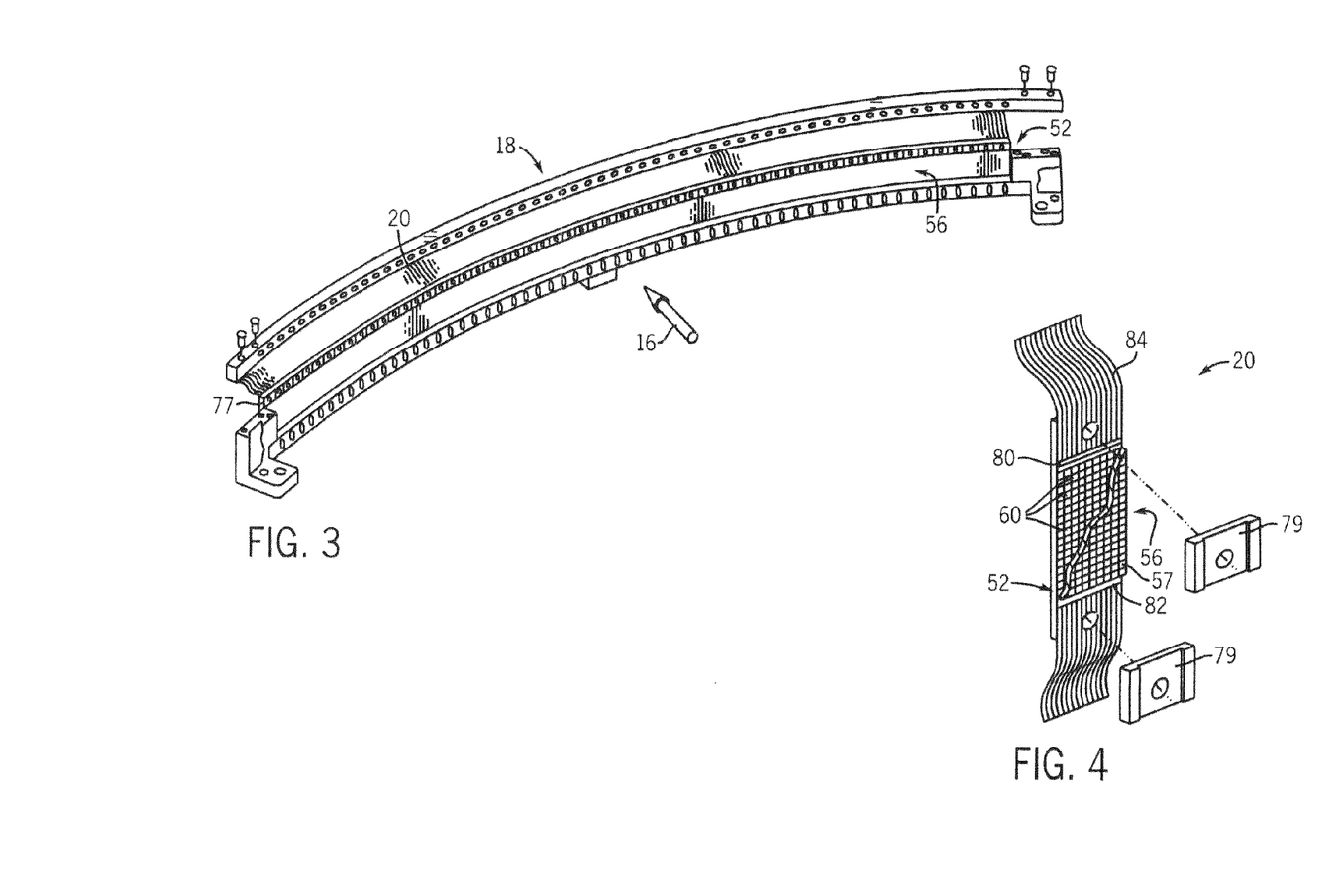
FIG. 3 is a perspective view of one embodiment of a CT system detector array.
FIG. 4 is a perspective view of one embodiment of a detector.

As shown in FIGS. 3 and 4, detector array 18 includes a plurality of scintillators 57 forming a scintillator array 56. A collimator (not shown) is positioned above scintillator array 56 to collimate x-ray beams 16 before such beams impinge upon scintillator array 56.

In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 84. Particularly, about one-half of photodiode outputs are electrically connected to switch 80 with the other one-half of photodiode outputs electrically connected to switch 82. Additionally, a reflector layer (not shown) may be interposed between each scintillator 57 to reduce light scattering from adjacent scintillators. Each detector 20 is secured to a detector frame 77, FIG. 3, by mounting brackets 79.

Switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

Figure 5:
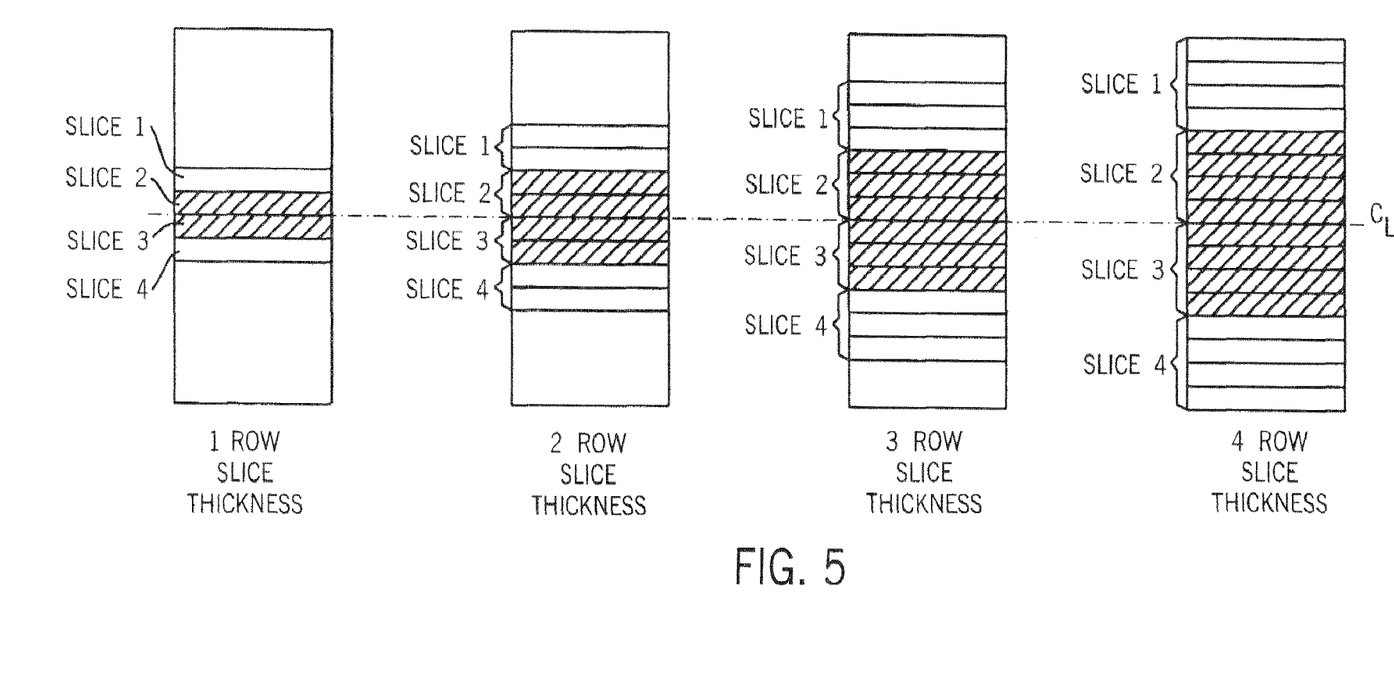
FIG. 5 is illustrative of various configurations of the detector in FIG. 4 in a four-slice mode.

As shown in FIG. 5, by transmitting the appropriate decoder instructions, switch arrays 80 and 82 can be configured in the four-slice mode so that the data is collected from four slices of one or more rows of photodiode array 52. Depending upon the specific configuration of switch arrays 80 and 82, various combinations of photodiodes 60 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

Figure 6:
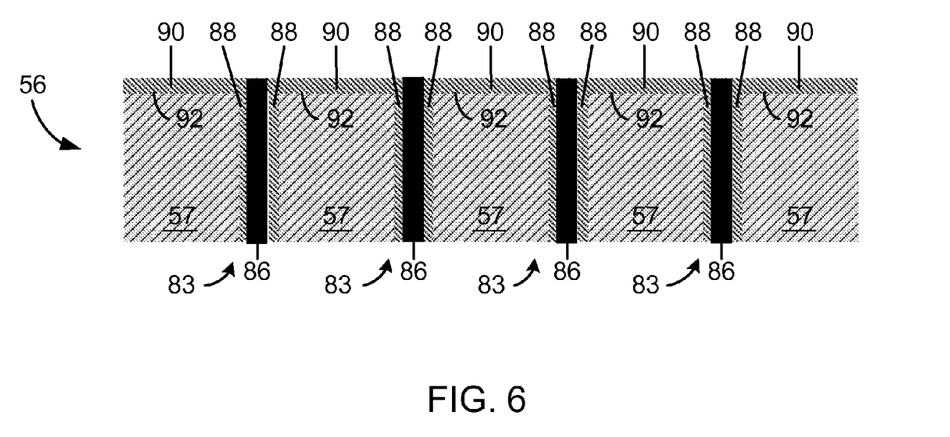
FIG. 6 is a schematic representation of a side view of a portion of a scintillator array in accordance with the present invention.

Referring now to FIG. 6, a cross-section of a portion of scintillator array is illustrated. As previously discussed, scintillator array 56 includes a plurality of uniformly spaced scintillators 57. Interstitially spaced or disposed between adjacent scintillators 57 is a reflector 83. The reflector 83 is designed to maintain a relatively high light output for each scintillator 57 as well as prevent light and x-ray cross-talk between scintillators 57. In this regard, each reflector 83 is composed, in one embodiment, of three layers. Specifically, a composite layer 86 is sandwiched between a pair of reflective layers 88. Preferably, the composite layers 86 are formed of a high atomic number metal and a low viscosity polymer. Examples of possible applicable high-Z metals include tungsten, tantalum, or other heavy metals which in powder form have a density greater than 16 g/cm$^3$. Any of a number of low viscosity commercially available epoxies, such polyurethane, may be used as the polymer component of the composite layers. While it is preferred that the polymer be dark in color to improve performance of the scintillator array, it is contemplated that lighter polymers may be used. That is, there is no color requirement for the polymer material. Additionally, it is preferred that the polymer be fabricated from a material that has a relatively high resistance to radiation.

In one preferred embodiment, the thickness of the metal composite layer 86 is approximately 50-100 μm. In contrast, each reflective layer 88 preferably has a thickness of approximately 15-50 μm. The metal composite layers 86 are designed to absorb light that is transmitted from one scintillator to an adjacent scintillator thereby reducing, if not eliminating, optical cross-talk between the scintillators. Additionally, the metal composite layers are configured to absorb x-ray photons translating between scintillators. The amount as well as type of materials used in the metal composite layers defines the light as well as x-ray stopping power. However, one particular composite has been shown to absorb up to 50% of the x-ray photons between scintillators thereby reducing x-ray cross-talk by 50%. Given that optical cross-talk is typically 45% and x-ray cross-talk is typically 55% of the total cross-talk, with this exemplary composition and in accordance with the present invention, the total cross-talk of the scintillator array would be reduced by approximately 20% to 30% versus a conventional reflector. Additionally, the metal composite layer greatly reduces x-ray punch-through, e.g. by 60% or more.

Still referring to FIG. 6, reflector layers 88 are formed from an epoxy loaded with titanium dioxide (TiO$_2$). The reflector layers 88 are generally opaque and are designed to prevent light emissions from each of the scintillators 57. That is, the reflector layers 88 operate to confine the light generated by each of the scintillators 57 to be within the respective scintillators 57. As such, light, ideally, is not transferred between adjacent scintillators 57. Since a photodiode is designed to detect light emissions from each of the scintillators 57, the reflector layers 88 are used to improve the convergence of light toward the photodiode and the metal composite layer 86 reduces x-ray cross-talk between adjacent scintillators 57. To further improve light collection efficiency, a reflector top coat or layer 90 is cast or otherwise deposited on the x-ray receptor surfaces or faces 92 of the scintillators 57 Coating 90 is designed to re-direct light emissions without affecting x-ray passage.

Figure 7:
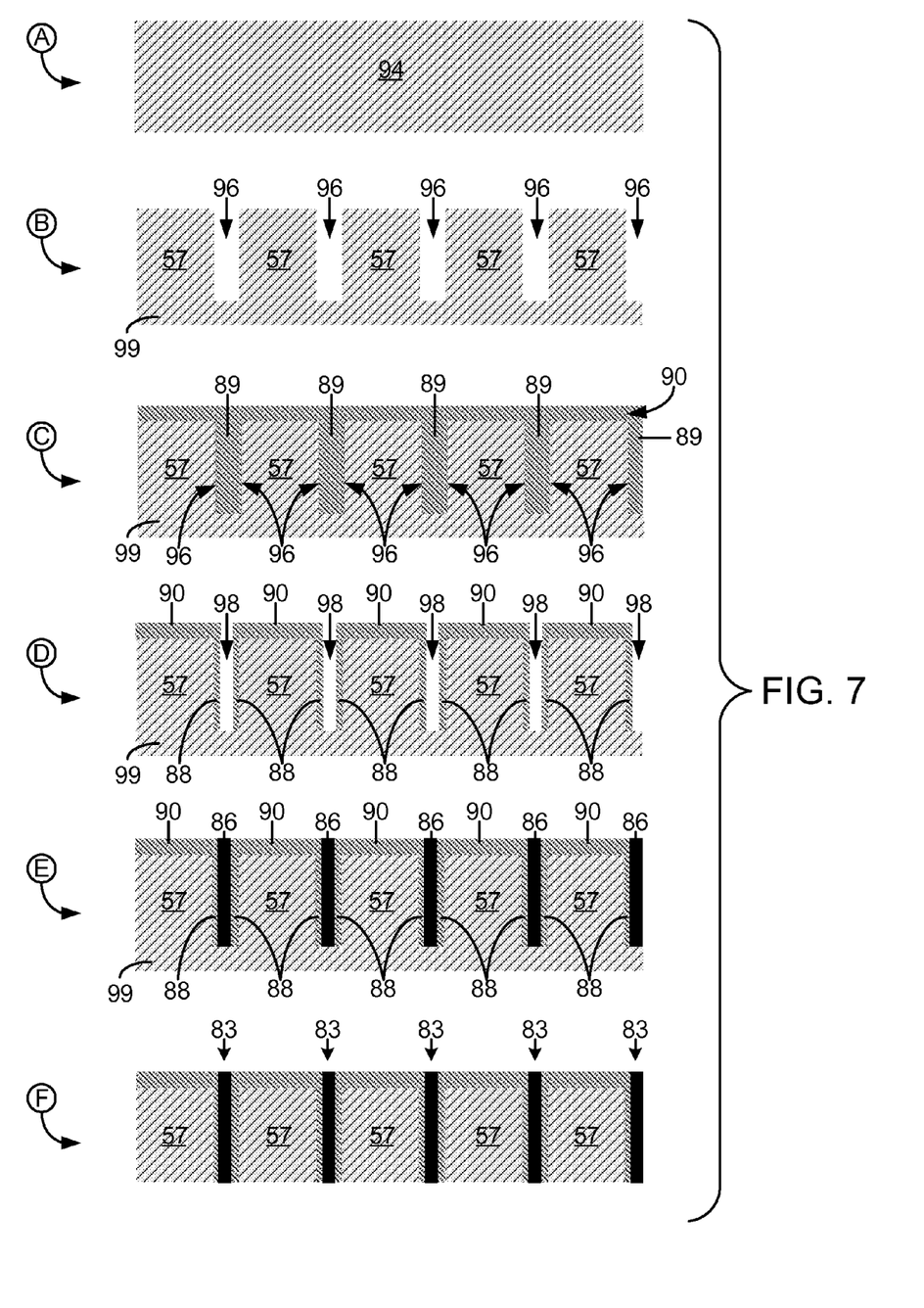
FIG. 7 is a graphical representation of a scintillator array manufacturing process in accordance with the present invention.

Refining now to FIG. 7, stages of a manufacturing technique in accordance with the present invention will be described in greater detail. Stage A of the manufacturing technique begins with the formation of a scintillator substrate 94. The scintillator substrate 94 is comprised of one or more materials designed to illuminate and output light upon the reception of x-rays or other radiographic imaging energy. The substrate 94 may be fabricated in accordance with one of a number of well-known semiconductor fabrication techniques. Stage A further includes grounding of the bulk substrate material into a wafer having a desired thickness as well as grinding or other processes to dimensionally define the substrate.

In Stage B of the manufacturing technique, the substrate 94 undergoes one of a number of pixelating processes to define a number of scintillators 57 in the substrate 94. For example, the substrate 94 may be diced using a wire saw dicer or other dicing mechanism. Additionally, the individual scintillators 57 may be defined using ion beam milling, chemical etching, vapor deposition, or any of other well-known substrate cutting techniques. Preferably, the individual scintillators 57 are defined such that a gap 96 is formed between adjacent scintillators. Additionally, the scintillators 57 are preferably defined two-dimensionally across the scintillator substrate 94. Preferably, gaps 96 extend between individual scintillators 57 in both the x and z directions and have a width of approximately 100 to 200 μm depending on the requirement of geometric dose efficiency. The depth of the gaps depends on the stopping power desired and varies according to scintillator substrate composition.

Following formation or definition of the individual scintillators 57, a highly reflective material 89 is preferably cast onto the scintillators 57 and into the gaps 96 defined therebetween in Stage C. In one preferred embodiment, the cast filler 89 contains approximately 40% to 70% by weight titanium dioxide. However, one skilled in the art will appreciate that the cast filler 89 is not limited to an epoxy having titanium dioxide. Other highly reflective materials such as $Ta_2O_5$, $HfO_2$, $Bi_2O_3$, and PbO, as well as other similar materials may also be used. While these materials typically do not have a reflectivity characteristic as high as titanium dioxide, these materials do have sufficient x-ray stopping power characteristics that assist in the reduction of x-ray cross-talk between scintillators. Moreover, one skilled in the art will appreciate that casting defines one particular means by which reflector material may be disposed between the scintillators. As such, the present invention contemplates other deposition processes including injection molding, for example.

Preferably, the highly reflective material 89 takes the form of a powder and is cast in gaps 96. As such, the powder is cured for a prescribed period. After curing, the top surface or portion of the scintillator array is machined to leave a top reflective layer 90 that has a desired thickness, e.g. 200 μm thick.

In Stage D, new gaps or channels 98 are created between scintillators 57 in the reflective material 89. Preferably, gaps 98 are created along both the x and z directions. Gaps 98 may be created using one of a number of cutting or dicing techniques as well as chemically-based etching processes. For example, gaps 98 may be formed using a wire saw or machining laser. Chemical etching, ion beam milling, as well as other semiconductor fabrication processes may also be implemented. In the example of a laser, a ND:YAG laser, $CO_2$ laser, or an AR$^+$ laser, or semiconductor laser may be used. In this example, the laser beam is focused on the center or middle of the reflective material disposed between the scintillators 57 and the width of the cut is adjusted so that a desired gap or channel width 98 results following the cutting process.

Wire saw dicing may also be used to machine gaps 98 in the reflective material 89 disposed between scintillators 57. For example, a wire having a diameter of 70 μm or less may be used to cut the desired gaps 98. In this regard, the wires are positioned on a spool (not shown) with a desired pitch. A mechanical fixture is then used to accurately position the wires and spool.

It is contemplated that at least two different types of wires may be used. That is, a metal wire with grinding media slurry feeding with the wires may be used. In this regard, the wires pass through the reflective material 89 and create the desired gaps. The grinding media may be diamond, SiC powder, alumina, and other well-known grinding media material. Preferably, the grinding media power has a grid size of 1,000 to 3,000 mesh. Another possible solution is to use a metal wire embedded with diamond or SiC media. OD (Outer Diameter) dicing saw may also be used. Regardless of the method, means, and mechanism to generate gaps 98, in a preferred embodiment, the thickness of the resulting reflective coating on the surface of each scintillator is approximately 15 to 50 μm.

Following formation of gaps 98 in the reflective material 89 between scintillators 57 so as to form a pair of separated reflective layers 88, a metal powder composite 86 is deposited into each gap 98 during Stage E. Preferably, the metal powder composite includes a high-Z metal such as tungsten or tantalum and is selected because of its high x-ray stopping power. Preferably, the metal powder of metal powder composite 86 has particular size of 0.5 to 5 μm. A low viscosity polymer such as epoxy, EpoTek® 301, polyurethane, or other low viscosity polymer is selected as a binder for metal powder composite 86. EPOTEK is a registered trademark of Epoxy Technology Inc. of Billerica, Mass. In this regard, 40% to 60% by volume of the metal powder is preferably homogeneously mixed with a liquid polymer. The mixture or composition 86 is then cast into gaps 98 created in the reflective material 89 of reflective layers 88. After casting, the mixture 86 is allowed to cure.

One skilled in the art will appreciate that other methods or techniques may be used to deposit the metal layer composition 86 between pairs of reflective layers 88. For instance, the high-Z metal particulars may be coated with an adhesive binder material such as a thermoplastic polymer coating. The coated metal particulars would then be cast into the gaps 98 with a small amount of solvent such as alcohol. The solvent may then be vaporized whereupon the resultant material is heated to melt the thermoplastic coating that will bind all the particulars together as well as serve as an adhesive between scintillators 57. Another method includes coating the high-Z particles with tungsten or with low temperature solder film. The solder film is then melted after being cast into the gap. After the film is formed, the scintillator array is ground or milled on the top surface to remove extra material of the metal composite and reflective material. Preferably, the top reflector 90 has a thickness of approximately 50 to 200 μm to maximize light output while minimizing x-ray attenuation.

Once the metal composite layer 86 interstitially disposed between pairs of reflective layers 88 is allowed to cure, the scintillator array is then machined at Stage F into a final and desired dimension. Additionally, the bottom surface 99 of the scintillator substrate is machined or ground to remove extra scintillator material and to attain a final and desired thickness. For example, depending on the type of scintillator being fabricated, the final thickness ranges from approximately 1.5 to 3 mm. The machined surface may then be optically coupled to a photodiode in accordance with well-known CT detector fabrication assembly.

Figure 8:
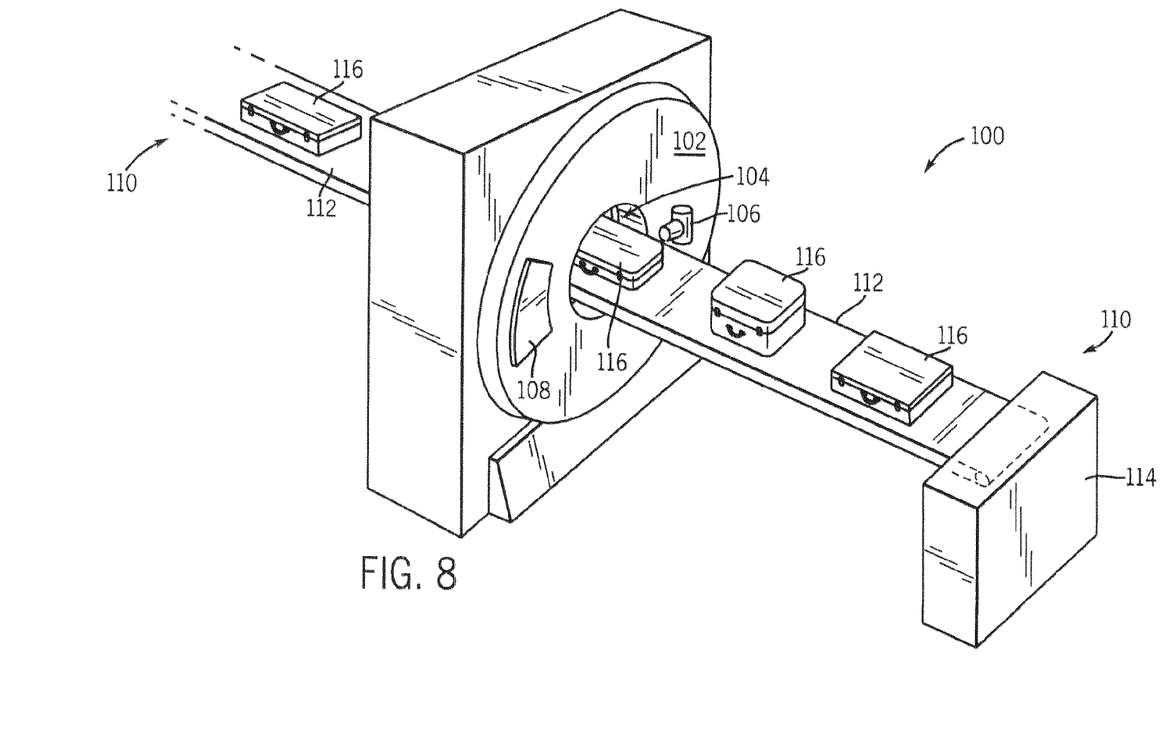
FIG. 8 is a pictorial view of a CT system for use with a non-invasive package inspection system.

Referring now to FIG. 8, package/baggage inspection system 100 includes a rotatable gantry 102 having an opening 104 therein through which packages or pieces of baggage may pass. The rotatable gantry 102 houses a high frequency electromagnetic energy source 106 as well as a detector assembly 108 having scintillator arrays comprised of scintillator cells similar to that shown in FIG. 6 or 7. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc.

The present invention has been described with respect to fabricating a multi-layer reflector disposed between scintillators of a CT detector for a CT-based imaging system. Further, fabrication of a rectangular shaped scintillator has been described. However, the present invention contemplates additional patterns or shaped cells being fabricated and a multi-layer reflector being disposed between scintillator cells. Additionally, the present invention has been described with respect to reflectors that are cast along one dimension, i.e., the z-axis. However, the reflectors may be formed using the aforementioned methods of manufacturing along an x and z axis thereby rendering a "checkerboard" full two-dimensional (2D) arrangement of reflectors. The present invention may also be implemented to create a partial 2D array of reflectors.

Therefore, in accordance with one embodiment of the present invention, a CT detector includes a scintillator array having a plurality of scintillators and a reflector interstitially disposed between adjacent scintillators. The reflector includes a light absorption element disposed between a pair of reflective elements.

In accordance with another embodiment of the present invention, a CT system is provided and includes a CT detector array having a scintillator array configured to illuminate upon reception of radiographic energy. The CT detector array further includes a reflector element disposed between adjacent scintillators of the scintillator array. Each reflector element includes a composite layer sandwiched between at least a pair of reflective layers.

According to another embodiment of the present invention, a method of CT detector manufacturing is provided. The method includes the steps of providing a scintillator array of a plurality of scintillators and disposing a reflective layer between adjacent scintillators. The manufacturing method further includes the step of disposing a composite layer in the reflective layer.

The present invention has been described in terms of the preferred embodiment, and it is recognized that equivalents, alternatives, and modifications, aside from those expressly stated, are possible and within the scope of the appending claims.

What is claimed is:

1. CT detector comprising:
   a scintillator array having a plurality of scintillators;

a reflector interstitially disposed between at least two adjacent scintillators, the reflector including a light absorption element disposed between a pair of reflective elements; and a reflective layer coated to a top face of the scintillator array, wherein the light absorption element extends in length to an upper surface of the reflective layer.

2. The CT detector of claim 1 wherein the light absorption element is configured to reduce optical cross-talk between the at least two adjacent scintillators.

3. The CT detector of claim 2 wherein the light absorption element is configured to substantially eliminate optical cross-talk between the at least two adjacent scintillators.

4. The CT detector of claim 1 incorporated into a CT imaging system.

5. The CT detector of claim 4 wherein the CT imaging system is configured to acquire radiographic data of a medical patient.

6. The CT detector of claim 1 wherein the reflector interstitially disposed between at least two adjacent scintillators is a composite comprising a high atomic number metal and a low viscosity polymer.

7. The CT detector of claim 6 wherein the low viscosity polymer is one of epoxy and polyurethane.

8. The CT detector of claim 6 wherein the high atomic number metal is one of tungsten and tantalum.

9. The CT detector of claim 6 wherein the high atomic number metal has a density greater than 16 g/cm^3.

10. A CT system comprising:
   a rotatable gantry having a bore centrally disposed therein;
   a table movable fore and aft through the bore and configured to position a subject for CT data acquisition;
   a high frequency electromagnetic energy projection source positioned within the rotatable gantry and configured to project high frequency electromagnetic energy toward the subject; and
   a detector array disposed within the rotatable gantry and configured to detect high frequency electromagnetic energy projected by the projection source and impinged by the subject, the detector array including:
   a scintillator array configured to illuminate upon reception of radiographic energy;
   a reflective top coat cast on an x-ray receptor surface of the scintillator array;
   a reflector assembly disposed between adjacent scintillators of the scintillator array; and
   wherein each reflector assembly includes a composite layer sandwiched between at least a pair of reflective layers;
   wherein the composite layer extends in length to an upper surface of the reflective top coat; and
   wherein the composite layer includes a high-Z metal and a low-viscosity polymer.

11. The CT system of claim 10 wherein the high Z-metal includes one of tungsten and tantalum.

12. The CT system of claim 10 wherein the low-viscosity polymer has a non-translucent color.

13. The CT system of claim 10 wherein the at least a pair of reflective layers includes $TiO_2$.

14. The CT system of claim 10 wherein each reflective layer has a lateral thickness of approximately 15-90 μm and the composite layer has a lateral thickness of approximately 50-100 μm.

15. The CT system of claim 10 wherein the reflector assembly is cast between adjacent scintillators.

16. The CT system of claim 10 wherein the composite layer is an optical light absorber.

17. The CT system of claim 10 wherein the composite layer further comprises a low viscosity polymer.

18. The CT system of claim 17 wherein the low viscosity polymer is one of epoxy and polyurethane.

19. The CT system of claim 10 wherein the high-Z metal comprises one of tungsten and tantalum.

20. A method of CT detector manufacturing comprising the steps of:
   providing a scintillator array of a plurality of scintillators, wherein the step of providing a scintillator array includes the step of forming a substrate of scintillation material;
   disposing a reflective layer between adjacent scintillators;
   disposing a reflective layer directly on an x-ray receptor surface of the scintillator array;
   disposing a light absorbing composite layer between the reflective layers that are disposed between adjacent scintillators;
   pixelating the substrate, wherein the step of pixelating includes at least one of chemically and mechanically forming gaps in the substrate to define the plurality of scintillators;
   depositing reflective material into at least the gaps; and
   wherein the step of disposing a composite layer in the reflective layer includes the step of creating channels in the reflective material.

21. The method of claim 20 wherein mechanically forming gaps includes dicing the substrate.

22. The method of claim 20 wherein the step of depositing includes the step of casting.

23. The method of claim 20 wherein the step of creating includes at least one of laser cutting, wire cutting, and etching.

24. The method of claim 20 further comprising the step of depositing composite material into the channels.

25. The method of claim 24 wherein the composite material includes a metal and a polymer.

26. The method of claim 24 wherein the step of depositing composite material into the channels includes casting.

27. A CT detector comprising:
   a scintillator array having a plurality of scintillators;
   a reflective top coat cast on an x-ray receptor surface of each of the plurality of scintillators; and
   a reflector interstitially disposed between at least two adjacent scintillators, the reflector including a light absorption composite element disposed between a pair of reflective elements, wherein the light absorption composite element extends in length to an upper surface of the reflective top coat, and wherein the light absorption composite element is configured to absorb x-rays.

28. The CT detector of claim 27 wherein the light absorption composite element is further configured to absorb approximately 50% of the x-ray photons across a gap between the at least two adjacent scintillators.

29. A CT detector comprising:
   a scintillator array having a plurality of scintillators;
   a reflective top coat cast on an x-ray receptor surface of each of the plurality of scintillators; and
   a reflector interstitially disposed between at least two adjacent scintillators, the reflector including a light absorption element disposed between a pair of reflective elements wherein the light absorption element extends in length to an upper surface of the reflective top coat, and wherein the light absorption element is configured to reduce x-ray punch through.

30. A CT detector comprising:
a scintillator array having a plurality of scintillators;
a reflective top coat cast on an x-ray receptor surface of each of the plurality of scintillators; and
a reflector interstitially disposed between at least two adjacent scintillators, the reflector including a light absorption element disposed between a pair of reflective elements wherein the light absorption element extends in length to an upper surface of the reflective top coat, and wherein the light absorption element includes a high atomic number metal composite.

31. The CT detector of claim 30 wherein the metal composite includes a cured metal powder and low viscosity polymer combination.

32. The CT detector of claim 31 wherein the polymer includes polyurethane.

33. The CT detector of claim 30 wherein the metal composite includes at least one of tungsten, tantalum, and a metal powder with density greater than 16 g/cm$^3$.

34. A CT detector comprising:
a scintillator array having a plurality of scintillators;
a reflective top coat cast on an x-ray receptor surface of each of the plurality of scintillators; and
a reflector interstitially disposed between at least two adjacent scintillators, the reflector including a light absorption element disposed between a pair of reflective elements wherein the light absorption element extends in length to an upper surface of the reflective top coat, and wherein the pair of reflective elements include TiO$_2$.

35. A CT system comprising:
a rotatable gantry having a bore centrally disposed therein;
a table movable fore and aft through the bore and configured to position a subject for CT data acquisition;
a high frequency electromagnetic energy projection source positioned within the rotatable gantry and configured to project high frequency electromagnetic energy toward the subject; and
a detector array disposed within the rotatable gantry and configured to detect high frequency electromagnetic energy projected by the projection source and impinged by the subject, the detector array including:
a scintillator array configured to illuminate upon reception of radiographic energy;
a reflective top coat cast on an x-ray receptor surface of the scintillator array;
a reflector assembly disposed between adjacent scintillators of the scintillator array; and
wherein each reflector assembly includes a first light absorptive layer sandwiched between at least a pair of reflective layers wherein the first light absorptive layer extends in length to an upper surface of the reflective top coat; and
wherein the at least a pair of reflective layers includes TiO$_2$.

36. A CT system comprising:
a rotatable gantry having a bore centrally disposed therein;
a table movable fore and aft through the bore and configured to position a subject for CT data acquisition;
a high frequency electromagnetic energy projection source positioned within the rotatable gantry and configured to project high frequency electromagnetic energy toward the subject; and
a detector array disposed within the rotatable gantry and configured to detect high frequency electromagnetic energy projected by the projection source and impinged by the subject, the detector array including:
a scintillator array configured to illuminate upon reception of radiographic energy;
a reflective top coat cast on an x-ray receptor surface of the scintillator array;
a reflector assembly disposed between adjacent scintillators of the scintillator array; and
wherein each reflector assembly includes a first layer comprising a high atomic number metal and a low viscosity polymer, the first layer sandwiched between at least a pair of reflective layers, and wherein the first layer extends in length to an upper surface of the reflective top coat; and
wherein each reflective layer has a lateral thickness of approximately 15-90 μm and the composite layer has a lateral thickness of approximately 50-100 μm.

37. A CT system comprising:
a rotatable gantry having a bore centrally disposed therein;
a table movable fore and aft through the bore and configured to position a subject for CT data acquisition;
a high frequency electromagnetic energy projection source positioned within the rotatable gantry and configured to project high frequency electromagnetic energy toward the subject; and
a detector array disposed within the rotatable gantry and configured to detect high frequency electromagnetic energy projected by the projection source and impinged by the subject, the detector array including:
a scintillator array configured to illuminate upon reception of radiographic energy;
a reflective top coat cast on an x-ray receptor surface of the scintillator array;
a reflector assembly disposed between adjacent scintillators of the scintillator array; and
wherein each reflector assembly includes a first layer sandwiched between at least a pair of reflective layers, the first layer including a low viscosity polymer comprising one of epoxy and polyurethane, and wherein the first layer extends in length to an upper surface of the reflective top coat; and
wherein the reflector assembly is cast between adjacent scintillators.

* * * * *